United States Patent [19]

Siu

[11] Patent Number: 5,420,689
[45] Date of Patent: May 30, 1995

[54] HIGH SPEED ILLUMINATION SYSTEM FOR MICROELECTRONICS INSPECTION

[76] Inventor: Bernard Siu, 732 N. Diamond Bar Blvd., Diamond Bar, Calif. 91765

[21] Appl. No.: 25,441

[22] Filed: Mar. 1, 1993

[51] Int. Cl.$^6$ .............................................. G01B 11/24
[52] U.S. Cl. ................................... 356/394; 356/376
[58] Field of Search ................ 356/394, 237, 375, 376

[56] References Cited

U.S. PATENT DOCUMENTS

| | | | |
|---|---|---|---|
| 3,737,226 | 6/1973 | Shank | 355/67 |
| 4,427,880 | 1/1984 | Kanade et al. | 356/4 |
| 4,508,452 | 4/1985 | DiMatteo | 356/375 |
| 4,568,835 | 2/1986 | Imamura et al. | 356/446 |
| 4,695,163 | 9/1987 | Schacher | 356/369 |
| 4,791,482 | 12/1988 | Barry et al. | 356/375 |
| 4,876,455 | 10/1989 | Sanderson | 356/376 |
| 4,972,493 | 11/1990 | Chemaly | 382/8 |
| 4,988,202 | 1/1991 | Nayar et al. | 356/376 |
| 5,027,418 | 6/1991 | Ikegaya et al. | 250/562 |
| 5,030,008 | 7/1991 | Scott et al. | 356/394 |
| 5,302,836 | 4/1994 | Siu | 250/572 |

Primary Examiner—Robert P. Limanek
Assistant Examiner—David B. Hardy
Attorney, Agent, or Firm—Leo R. Carroll

[57] ABSTRACT

This invention is a high speed illumination apparatus and technique which highlights bond wires, ball bonds, bond wedges and microcircuit chips separately against a similar substrate background for manual or high speed automatic inspection of microelectronics assemblies. Preferred angles of illumination are provided which reflect off the different specular surfaces of the bond wires, wire bonds, and bond wedges, providing improved background contrast. Light projected on the flat surfaces of microchip bodies tends to be absorbed, producing a negative contrast shadow if the other elements are illuminated in parallel. Formation of the multiple light rings starts with light generated by a tungsten lamp, collimation by a condenser lens, then passage through a liquid crystal light valve having a plurality of circular active transmission areas. A projector lens receives both rings of light and projects the larger ring on an ellipsoidal reflector which redirects the light onto the microcircuit at the large off-verical axis angle. The projector lens also focuses the more narrow beam of light on a torroidal Fresnel lens mounted above the microcircuit, and which also redirects the beam at the smaller off vertical axis angle. By alternating the light transmission through each of these rings at high speed, reflective signatures of interconnect wires, ball bonds, bond wedges and microcircuit chips can be captured by the an objective lens and mirror reflected to light responsive cameras. When displayed, the resulting unique signatures are easily distinguishable.

10 Claims, 3 Drawing Sheets

HIGH SPEED ILLUMINATION SYSTEM FOR MICROELECTRONICS INSPECTION

BACKGROUND OF THE INVENTION

1. Technical Field

This invention relates generally to methods and apparatus for high speed inspection of microelectronic device connections, and in particular to equipments used to illuminate interconnect wire bonds, ball bonds, and wedge bonds so as to improve discrimination against similar appearing backgrounds. This invention is related to application U.S. Ser. No. 914,541, now U.S. Pat. No. 5,302,836, which describes an earlier embodiment of this invention. That application included a multiple ring illumination system comprised of separate cylindrical fiber optics bundles which were angled and shutter switched to provide light at incident angles optimal for improved discrimination. See FIGS. 3-6 of U.S. Pat. No. 5,302,836. This invention further improves operational speed by replacing the fiber optics and shutter with a liquid crystal light valve assembly.

Typically, gold wires, gold bonds, and gold terminations are viewed against a gold background by manual inspection under a microscope. Since the field of view is normally less than one-eighth ($\frac{1}{8}$) of an inch, uniform illumination is needed to highlight the area of interest. The most common uniform illumination source is a circular ring light directing illumination perpendicularly or at a slight angle off normal onto the surface to be inspected. While this type of lighting works rather well under a microscope, the glares and shiny hot spots from the gold connections and the reflective backgrounds are often ignored by the operators, and they tend to interpolate, or "fill in" dark missing fragments of the images. Variations in such human judgments are a cause of inconsistent inspection results. For instance, the incremental fill in of a dark position on a wire may actually hide a break in the wire at that point.

With the recent development of machine vision technologies, attempts were made to inspect these gold interconnects and gold terminations per Mil-Std-883 Method 2017. Machine vision technologies, however, have not reached the sophistication of ignoring hot spots or filling in fragments in a random basis as a human being could. The approach, therefore is to develop an illumination technique, capable of isolating the specular interconnect wires, ball bonds, bond wedges and chips exclusively from its reflective backgrounds. In other words, provide a better contrast between the object of interest from its neighboring background. In addition, the illumination techniques must be fast enough to support machine vision technologies used for the image acquisition and processing of microelectronics inspection tasks.

2. Background Art

Early improvements in inspection methods were concerned with better work-piece illumination, more accurate location, object image acquisition, flaw identification, recognition and finally rejection against given criterion. The focus of evolutionary inventive steps in these directions may be seen by overview of the following patents:

The need for diffused lighting to reduce reflections and shadows in close-up photography has been long recognized. Shank, in U.S. Pat. No. 3,737,226 discloses apparatus in which an indirect light source illuminates a small object through a series of pyramidal reflectors. Light is thus diffused around four sides of the object before reflection to a camera. This invention was for close-up photography and would have limited value for high speed inspection of microelectronic elements.

Kanade et al., in U.S. Pat. No. 4,427,880, provide an array of discrete light-emitting sources which are used to sequentially illuminate a symmetrical work piece object. Reflections are focused on a light responsive position sensor so as to provide continuous indications of distance, surface orientation and curvature of the object. Details of surface geometry are not provided. This approach is most effective for measuring distance if the reflective surface is flat. Based on the position of the reflected light spots on the surface, the distance between the surface and the optical sensor can be calculated and determined. The system does not use continuous illumination for visual identification of the object and its orientation. U.S. Pat. No. 4,508,452 to DiMatteo et al provides for determining the surface profile of an object by projecting a pre-coded pattern onto the surface. By matching the newly acquired image pattern to a pre-determined image pattern, the profile of the newly acquired image can be extracted. An object surface is scanned by a moving projector and subdivided into the large number of coded sections. Comparisons are made of progressive photographs of the work-piece with those of a standard reference surface. The entire surface of an object may therefore be mapped. The system is not applicable to improving contrast between very small three dimensional objects, such as wires, and the reflective background.

Imamura et al. in U.S. Pat. No. 4,568,835, detects foreign matter such as dust particles on a plane substrate by means of scattering of the reflections from a laser beam. As a specimen work-piece such as a photomask is scanned by an oblique incidence laser illumination beam, reflections from foreign materials are less directly scattered than are those from the edges of the circuit pattern. The illumination incidence angle is 80 to 60 degrees off normal, with a portion of the beam being reflected from the substrate surface while the remainder is refracted into the substrate medium from which it is internally reflected then externally scattered outward. This approach does not consider circular illumination used with a highly reflective, low refractive background medium.

In a different surface measurement application, Schachar, in U.S. Pat. No. 4,695,163, determines the contour of a cornea by scanning the surface with coherent light from different positions along a rectilinear path. Reflections received by detectors along the track are maximally polarized when the incidence angle equals Brewsters's angle. From a knowledge of the index of refraction of the medium and of Brewster's angle, the relative spacial locations of points over the surface may be determined. The system should provide slow but precise information when a refracting medium is under inspection, but will have limited utility with highly reflective objects.

An object locating system for use with robotic systems is described in U.S. Pat. No. 4,791,482 to Barry et al. The system projects a known geometrical image from a light source onto the surface of an object. The plane of the image on the object is determined by finding a normal to the surface from known geometrical relationships. Comparison of normals at different surface points are used to calculate distances and angles between the points. Gaussian images are generated for comparison between referenced objects and the unit under test.

In the field of solder joint inspection systems, Sanderson in U.S. Pat. No. 4,876,455 discloses a fiber optic solder joint inspection approach, in which light from multiple sources is reflected from a specular object to a fixed array of transducers. The individual light sources are derived from a single source which is scanned and piped to a plurality of optical fibers which lead to individual openings spaced around a semicircular illumination frame. For a given surface attitude, reflections to the fixed transducers will result from only one illumination source, assuming essentially specular reflection from the surface. Given known surface features of the object, an approximate reconstruction of the shape is made. The point source is usable with solder joint fillet inspection, but not with the variably curved and positioned wiring connections of microelectronic assemblies.

A related invention, U.S. Pat. No. 4,988,202 to Nayar et al, extends the above approach to include generation of an Extended Gaussian Image representation of a solder joint which is then evaluated as to acceptability.

A system for inspection of the uniformity of the surface of a flat circuit board component such as a dual inline package, employing computer vision is taught by Chemaly in U.S. Pat. No. 4,972,493. Illumination is provided by low angular light at the surface edge. Anomalies on the flat surface of dual in-line packages are inspected for pits, holes, blisters, grease, marks, chips and cracks. Marks on the surface are distinguished from planned surface irregularities by comparison of grey scale brightness. The two directional lighting is not developed for specular surfaces such as wires, bonds and wedges.

Inspection of the circuit board components when soldered in place is taught by Ikegaya et al. in U.S. Pat. No. 5,027,418. Component lighting is provided by a standard ring illuminator positioned normal to the board. Board masking is provided to make an assessment of soldering condition independent of component lead placement on the circuit board lands.

It may be noted that none of the above inspection systems treat identification and inspection of variably curved and placed circuit elements such as microelectronic wires and bonds. Further, none teach the use or advantages of dual annular illumination sources, each disposed at different angular relationships with respect to normal, each of which provides optimal viewing contrasts for different classes of microelectronic wires and bonds relative their similar background.

DISCLOSURE OF INVENTION

The present invention is directed to improved systems for inspection of microelectronic assemblies, including the interconnect wires, ball bonds, and wedge bonds contained therein. Inspection of such devices today often uses a comparative method. Magnified projections of a reference sample and of the unit under inspection are visually compared on adjacent or split screens. The human inspector visually does the comparison and makes a subjective pass or fail judgement based upon their experience and training. The method is time consuming and produces inconsistent inspection results.

Replacement of the human operator with an automatic inspection machine involves overcoming three (3) major obstacles. The first obstacle is to be able to "see" and isolate objects of interest from their background. The degree of contrast must be great enough for a machine vision technology to isolate and identify. For instance, gold wires, gold wire bonds, and gold wedges must be contrasted against gold or similar backgrounds in a manner somewhat similar to that used by a human inspector to acquire the image. The second obstacle is to make pass or fail decisions based upon perceptions of the acquired image. The final obstacle is to repeatedly solve the first two problems at a rate beyond the capability of the human operator.

This invention comprises high speed illumination apparatus for highlighting the specular surfaces of interconnect bond wires, ball bonds, bond wedges and microcircuit chips commonly used in microelectronics assemblies.

Apparatus for implementing this invention includes multiple concentric rings of illumination from which light is directed toward the center of the rings. In operation, the area of interest on the microcircuit assembly is placed directly under the focused center of these concentric rings. The angle of incidence for each of these rings is unique, one for interconnect bond wires and ball bonds, while the other is for bond wedges. The combination of both rings is used for isolating microcircuit chips. As light is transmitted via the first ring, an annular layer of illumination is transmitted and focused onto the microcircuit surface from a predetermined angle of incident. Light from this angle of incidence reflects off the specular surface of the bond wires and ball bonds, presenting unique reflective signatures to an array of light responsive transducers, such as video cameras which are arranged to view along the vertical axis through the concentric centers of the ring lights. Similarly, when a second ring is energized, unique reflective signatures on the bond wedges are created. Finally, energizing both of the rings simultaneously, the non-reflective surfaces of the microcircuit chips can be distinguished amongst its reflective neighboring surfaces.

It has been determined that optimal angles of incidence relative to the tangent of the reflective surface can be found for different classes of objects. Since the reflective surface of the bond wire is cylindrical, for instance, illumination from any angle should produce the same reflective result to the video camera. Limitations arise however, when one has to consider the gold conductor traces the bond wires have to bridge over. These conductor traces form a gold background which have approximately the same reflective angle as the gold wires, thereby causing the bond wires to "disappear" into its background. It is found in this invention that by lowering the angle of transmission to between 75 and 85 degrees from the vertical axis, light reflected from conductor trace surfaces is directed away from the video camera, while the light reflected from part of the cylindrical surface reflects directly to the video camera, providing a significant contrast between the bond wires over the conductive traces.

In the case of the wedge bonds, the physical feature is quite different than that of the cylindrical surface of the bond wire. Its features result from the stamping process in which the bond wire is pressed onto the gold surface by the capillary tube of a typical wire bonding machine. This stamping process flattens part of the cylindrical wire forming a flat reflective surface at the wedge site. This flattened reflective surface changes from the slope angle of the wire to that of the horizontal surface of the substrate. This sloped surface provides a mirror like reflective surface as well as a unique signature compared to that of a bond wire. It is expected that the optimal angle of light transmission will be different relative to the round wire. It has been found in this invention that, by shifting the light transmission angle to between 25 and 35 degrees from the vertical axis, optimal contrast between the wedge reflective surface and the conductive traces can be obtained.

Highlighting the microcircuit chip exclusively from the bond wires, wedges and balls is achieved by using the reflectivity differences between their surfaces. Microcircuit chips have a rough surface and are black in color, therefore, reflects a minimum amount of light. By transmitting full illumination through both ring lights, all areas around the chip are flooded with light while the microchip remains as a dark object. The outline of this microchip is acquired by the video camera for determination of the chip location, orientation, shape and size as necessary.

Formation of the multiple light rings starts with light generated by a tungsten lamp, collimation by a condenser lens, then passage through a liquid crystal light valve having a plurality of circular active transmission areas. A projector lens receives both rings of light and projects the larger ring on an ellipsoidal reflector which redirects the light onto the microcircuit at the large off-vertical axis angle. The projector lens also focuses the more narrow beam of light on a torroidal Fresnel lens mounted above the microcircuit, and which also redirects the beam at the smaller off-vertical axis angle. By alternating the light transmission through each of these rings at high speed, reflective signatures of interconnect wires, ball bonds, bond wedges and microcircuit chips can be captured by the an objective lens and mirror reflected to the light responsive camera system transducers. Based on the known light speed and distances between our transmission source and light responsive cameras, elapsed time between transmission to image capture is calculated to be 3 nanoseconds. Our approach permits the alternating of illumination sources in less than 4 milliseconds using the computer controlled liquid crystal and reflector system. The speed of highlighting microelectronics components is therefore limited by the performance speed of managing illumination transmission through each of the light ring sources.

With the foregoing drawbacks of the prior art in mind, it is a prime object of the present invention to provide illumination methods and apparatus capable of improving the visual contrast between the interconnect wires, ball bonds, bond wedges and chips backgrounds.

It is another object of the invention to provide such contrast improvement when the items to be discriminated are made of a reflective material similar to that of the background, such as gold.

Yet another object of this invention is to provide a first annular concentric ring of illumination which focuses light at a first angle of incidence on centered microelectronic interconnect bond wires or ball bonds, so that their vertically reflected images will be visually sensed with a maximum contrast relative to their similar background reflections.

Still another object of the invention is to provide a second annular concentric ring of illumination which focuses light at a second angle of incidence on centered microelectronic bond wedges, so that their vertically reflected images will be visually sensed with a maximum contrast relative to their similar background reflections.

A further object of the invention is to provide two annular concentric rings of illumination, each of which focus light in combination at unique angles of incidence on centered non-reflective microelectronic chips, so that their vertically reflected outline images will be visually sensed with a maximum contrast relative to their background reflections.

An additional objective is to provide a high speed illumination system which is fast enough to support automatic machine vision equipments used for non contact image acquisition and processing of microelectronics inspection data.

An additional objective is to provide a high speed illumination and non contact image acquisition system which is fast enough to support automatic machine vision equipments used for processing of microelectronics inspection data.

The above and other objects, features and advantages of the present invention will become more apparent from the following description when making reference to the detailed description and to the accompanying sheets of drawings in which preferred structural embodiments incorporating the principals of this invention are shown.

BRIEF DESCRIPTION OF THE DRAWINGS

The details of my invention will be described in connection with the accompanying drawings, in which.

BEST MODE FOR CARRYING OUT THE INVENTION DESCRIPTION OF MICROELECTRONICS

Figure 1:
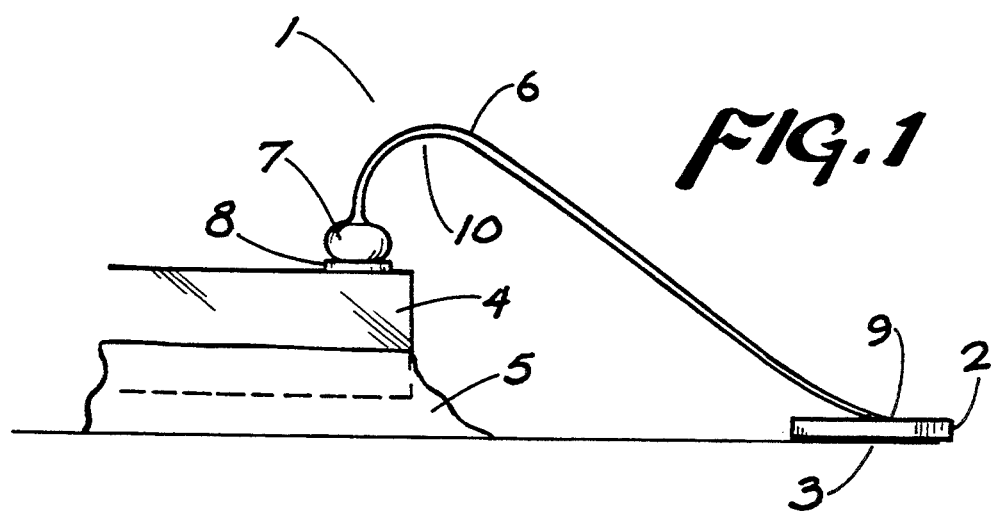
FIG. 1 is a partial side elevation view of a microelectronics assembly, showing a typical interconnection between a microcircuit chip and a conductor trace on a substrate.

Appreciation of the novelty of this invention starts with an understanding of common interconnection methods used in microelectronic assemblies. FIG. 1 is a partial side elevation view of such a microelectronics assembly, showing a typical interconnection between a microcircuit chip and a conductor trace on a substrate.

Figure 2:
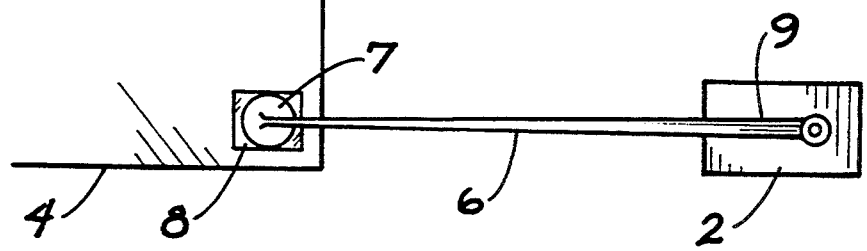
FIG. 2 is a partial top view of the typical interconnection depicted in FIG. 1.

FIG. 2 shows a partial top view of the same interconnection depicted in FIG. 1. Referring to FIGS. 1 & 2, microcircuit assembly 1 generally includes a typical conductive circuit pattern 2 printed on the surface of base substrate 3, usually made of a ceramic material. Microcircuit chip 4 is normally a cube-shaped integrated circuit which is attached onto substrate 4 using conductive or non-conductive epoxy 5. The electrical connection between the microchip circuit and the conductive traces on the substrate is made via cylindrical gold wire 6, typically 0.001 inch in diameter. The attachment of one end of the wire onto the microchip surface takes the shape of a flattened gold ball 7, subsequently named a ball bond. The bonding site for this attachment is called bond pad 8, and normally is a square conductive pad, situated along the edge of microchip 4. The opposite end of wire 6 is attached onto the surface of substrate conductive trace 2 by a stamping process, which results in the form of a flattened wedge 9, subsequently named a wedge bond. Since the surfaces of microchip 4 and the conductive pad 2 are at different heights, the bond wire 6 takes the form of a wire loop 10 between the two connections. This loop assures that bond wire 6 is prevented from touching the edge of the microchip 4, as well as providing adequate stress relief for the bond wire in the event of severe thermal stress and vibrations. Though ball bonds 7, bond wires 6, and bond wedges 9 are unique in their physical shape, they all possess highly specular surfaces. This invention, takes advantage of their specular surfaces and unique reflective signatures, and has provided apparatus and methods for presenting these images to light responsive transducers at high speed.

ILLUMINATION CONCEPTS

Applying known physics principles of reflectivity, we know that for a reflective surface, the angle of reflection is equal to the angle of in incidence, measured from the axis perpendicular to the tangent of the surface. Under usual inspection circumstances, illumination is directed onto the microelectronics surfaces perpendicularly. The light striking the bond wires, ball bonds, and bond wedges scatters in all directions due to their specular and cylindrical surfaces. The gold conductor traces lying in the background also produce scattered light rays, the majority of which are directed vertically back toward the light source because the conductor trace surfaces are relatively flat. These reflected light are the main causes of misinterpretation of images by imaging machines as well as human operators. A key to this invention is the determination of the optimal angles of incidence for the bond wires, ball bonds and wedge bonds, such that maximum contrast between the objects and their neighboring background can be achieved.

Figure 3:
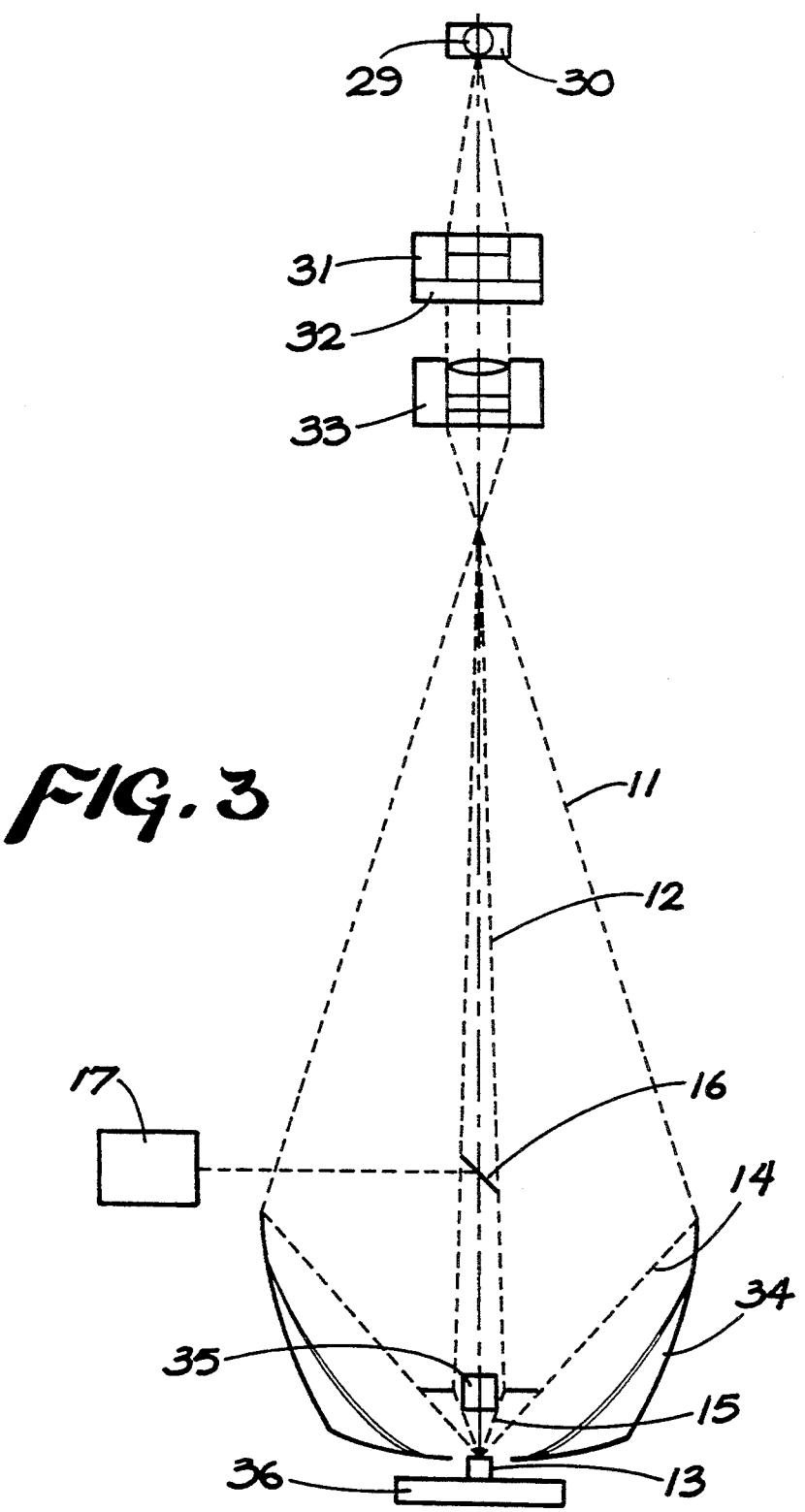
FIG. 3 is a side cross-section view of the arrangement of the optical elements of the illumination system.

As indicated in FIG. 3, this embodiment includes two light beams 11 and 12 affixed at selected angles from the objects of interest 13 such that light beams 14 and 15 strike these objects of interest at the desired angles and are reflected by mirror 16 to the CCD array of solid state camera system 17. By feeding light into these sources sequentially or simultaneously, different objects can be highlighted and received by the camera respectively. For example, to highlight the bond wires and ball bonds, light beam 15 is best provided at an illumination angle of 75 to 85 degrees from horizontal. On the other hand, if best illumination of the wedge bonds is desired, light beam 14 should be provided at 25 to 35 degrees. Similarly, if the chips need to be highlighted, both the lights are illuminated.

The basic design of the illuminator system is shown in the upper portion of FIG. 3. Light from lamp 30 is collimated by a cemented doublet condenser lens 31. The condenser lens 31 is positioned one focal length from the lamp, thus collimating the light from the lamps filament 29. The degree of collimation is set by the size of the filament 29.

Since the angle of arrival of the illumination light relative to a normal to the object surface varies between 30 and 82.5 degrees, liquid crystal means 32 are furnished in order to form and switch the two light beams. The liquid crystal output is imaged by a biconvex and cemented doublet projector lens 34 onto an elliptical reflector 34 for production of the larger incidence angles 14 off-normal. Since the elliptical reflector 34 is not capable of producing angles of incidence less than approximately 50 degrees, a second optical system must be used for the smaller angles. A Fresnel lenses element is positioned in a plane just above the objective lens, where it can redirect light on the workpiece at the smaller off-normal angles 15.

Reflected light from the microcircuit workpiece 13 is colinearly collected directly above the workpiece and is focused and redirected to camera system 17 by means of objective lens 35 and mirror 16. This arrangement provides flexibility in off axis placement of the camera elements.

Figure 4:
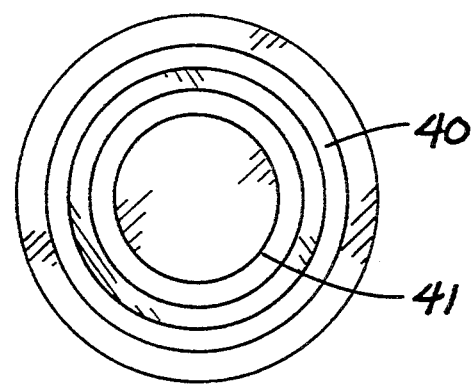
FIG. 4 is a top view of the concentric ringed liquid crystal light valve.

FIG. 4 illustrates a top view of liquid crystal light valve 32, which is placed just beyond condenser lens 31. Light valve 32 consists of a twisted nematic LCD cell, which has two continuous unpatterned electrodes, and two transmissive polarizing sheets, one sheet acting as polarizer, and the other as analyzer, not shown. In the natural state, the liquid crystal cell twists the passing light 90 degrees, however, the twisting power can be nullified by applying an electric field. Therefore, by placing the liquid crystal cell between a polarizer and an analyzer, the light valve that can be turned on and off directly by electronic means. This unit has two individually computer addressable concentric circular active regions 40,41 thus enabling two distinct radial zones of light to propagate through the remainder of the illuminator system. The central section is blocked out in order to prevent unwanted illumination reaching the reflector or the workpiece.

Figure 5:
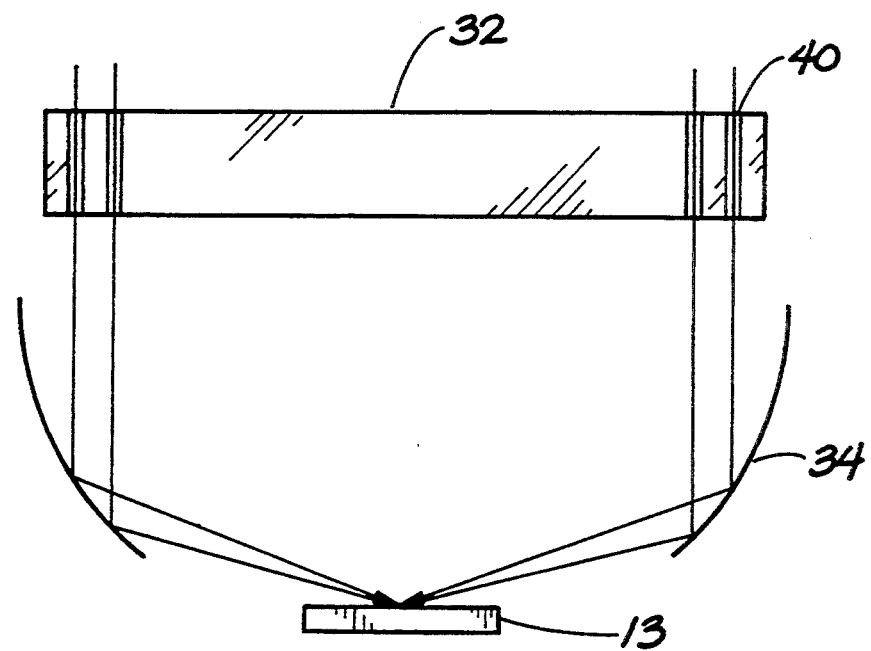
FIG. 5 is a side view of the liquid crystal light valve illuminating the microcircuit at the large off-axis angle via the reflector.

FIG. 5 shows a side view of the light valve 32, arranged to depict the wide angle illumination of ellipsoidal reflector 34 which redirects the beam on microcircuit 13 at the large off-vertical angle. The projector 33 and inner ring 41 have been removed from this view.

In summary, the preferred illuminator optical system consists of a condenser lens, a doublet projector lens, an ellipsoidal reflector for high angles of incidence illumination and Fresnel lenses for low angles of incidence. It is capable of illumination angles from approximately 17 to 83 degrees from normal. The optimum angles of illumination are selected using a liquid crystal light valve. The preferred embodiment light valve consists of three (3) independent rings which cab be energized by a system controller. As each ring is energized, a ring of light is allowed to pass through the light valve, striking at a predetermined location on the reflector. The transmitted illumination is then reflected to the area of interest at the desired predetermined angle. As different light valves are energized by the computer, different angles of illumination on the object can be rapidly achieved, thereby providing significant speed improvement over mechanical shutters.

Using the above angles of illumination and the claimed apparatus, highlighted bond wires have an image signature of a highlighted wire, ball bonds take the shape of a highlighted ball, bond wedges take a lighted shape similar to a triangle and a microchip takes the shape of a black block among white surroundings when projected onto a video monitor via a video camera. By using the threshold function of a machine vision system, the entire wire span can be further isolated from its background.

It should be noted that the system is not limited to inspection of microcircuits only. The high speed illumination technique can be used to control any predetermined illumination technique can be used to control any predetermined illumination for automated inspection systems. By modifying the angle of incident of the illumination, inspection of many other small items having specular surfaces, such as solder joints, component leads, or machine parts can be supported by this invention. As illustrated in FIG. 5, by increasing the number of rings on the liquid crystal light valve, more individual angles of light can be controlled by the computer at high speed. On the other hand, by increasing the width of the rings, a wider band of illumination on the object can be achieved at high speed.

The basic concepts of the techniques and apparatus for providing high speed illumination and the unique signatures of on microelectronics assemblies elements have been illustrated herein. Although the present invention has been described in considerable detail with reference to certain preferred embodiments thereof, other versions are possible. Therefore, the spirit and scope of the appended claims should not necessarily be limited to the description of preferred versions contained herein.

What is claimed is:

1. Illumination apparatus for inspection of microelectronic assemblies having internal microcircuit chips with terminals electrically connected by wire bonding means to circuit conductive traces on a mounting substrate, wherein chip bodies and interconnection elements including wires, ball bonds, and wedge bonds which must be visually discriminated against similar reflective backgrounds, comprising:

a plurality of concentric light ring source means for illumination of said chips and interconnect elements placed under a center of each said concentric light ring, wherein a first said light ring source is comprised of:

a common source of focused light;

condenser means for collimating light from said common source;

liquid crystal light valve means having a first active area means for forming a wide angle beam of light; and projection lens means for receiving and redirecting said wide angle beam of light from said liquid crystal light valve means;

a plurality of focusing means for directing each said light ring source at a predetermined angle of incidence relative to said microcircuit so that optimal contrast may be obtained between reflections from said chip bodies and interconnect elements and similar background trace reflections, wherein a first said focusing means comprises;

focusing means for receiving said wide angle beam of light from first said light ring source and redirecting said wide angle beam of light at an illumination angle off vertical which is sufficiently large so as to separate the reflections from said rounded inspection objects, including said bond wires and ball bond, from conductor background traces made of a similar material;

first optical means for collecting said light reflections from said chip bodies and interconnection elements emanating along a fixed axis through the concentric centers of each said light ring source and redirecting said reflections for viewing, and viewing means for visual inspection of said chip bodies and interconnect elements in order to determine bonding defects.

2. Illumination apparatus according to claim 1, wherein said first focusing means comprises an ellipsoidal reflector disposed so as to receive said wide angle beam of light and to redirect said beam on said microcircuit at said large incidence angle.

3. Illumination apparatus according to claim 1, wherein said plurality of concentric light ring source means further includes a second concentric light ring source comprised of:

said common source of focused light;

said condenser means for collimating light from said common source;

said liquid crystal light valve means having a second active area means for forming a narrow angle beam of light; and said projection lens means for receiving said narrow angle beam of light from said liquid crystal light valve means.

4. Illumination apparatus according to claim 3, wherein said focusing means further comprises second focusing means disposed so as to receive said narrow angle beam of light from said projection lens and to redirect said narrow angle beam of light on said microcircuit at an illumination angle off vertical which is sufficiently small so as to separate the reflection from inspection objects having variable sloped surfaces, including said wedge bonds, from substrate background traces made of a similar material.

5. Illumination apparatus according to claim 4, further comprising light switching means for sequential activation of illumination from each of said light ring sources.

6. Illumination apparatus according to claim 4, further comprising light switching means for simultaneous activation of said first and second light valve active area means so as to provide both the large incidence angle beam of light from said first focusing means and the small incidence angle beam of light from said second focusing means in order to separate reflections from inspection objects having flat body surfaces, including said chip bodies, from other substrate and inspection object background reflections.

7. Illumination apparatus according to claim 6, wherein both of said light switching means comprises electrical switching of said light valve means.

8. Illumination apparatus according to claim 7, wherein said large illumination angle is between 75 and 85 degrees off vertical.

9. Illumination apparatus according to claim 8, wherein said small illumination angle is between 25 and 35 degrees off vertical.

10. Illumination apparatus according to claim 9, wherein said interconnection elements and conductor background traces are made of gold.

* * * * *